(12) United States Patent
Dual et al.

(10) Patent No.: US 7,615,378 B2
(45) Date of Patent: Nov. 10, 2009

(54) PIPETTING NEEDLE

(75) Inventors: Jürg Dual, Zumikon (CH); Olivier Elsenhans, Sins (CH); Frank May, Zürich (CH)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 644 days.

(21) Appl. No.: 11/128,677

(22) Filed: May 13, 2005

(65) Prior Publication Data
US 2006/0286678 A1 Dec. 21, 2006

(30) Foreign Application Priority Data
May 14, 2004 (EP) .................... 04076436

(51) Int. Cl.
B01L 3/02 (2006.01)
G01N 1/10 (2006.01)

(52) U.S. Cl. .................. 436/180; 422/100; 422/105; 73/863.32; 73/864; 73/864.01; 222/198

(58) Field of Classification Search ............... 422/100, 422/105–108; 222/198, 200, 243; 73/863.32, 73/864, 864.01, 864.02, 864.24, 427; 436/180
See application file for complete search history.

(56) References Cited

U.S. PATENT DOCUMENTS

| | | | | |
|---|---|---|---|---|
| 4,974,458 | A * | 12/1990 | Koike ..................... | 73/864.25 |
| 5,005,434 | A * | 4/1991 | Watanabe et al. ......... | 73/864.21 |
| 5,582,798 | A * | 12/1996 | Meltzer .................. | 422/100 |
| 5,750,881 | A * | 5/1998 | Dorenkott et al. ......... | 73/37 |
| 5,919,706 | A * | 7/1999 | Tajima ................... | 436/54 |
| 6,003,388 | A | 12/1999 | Oeftering ................ | 73/864.01 |
| 6,232,129 | B1 | 5/2001 | Wiktor .................. | 436/180 |
| 6,296,811 | B1 | 10/2001 | Sasaki ................... | 422/100 |
| 6,869,571 | B2 * | 3/2005 | Ingenhoven et al. ....... | 422/100 |
| 6,874,699 | B2 * | 4/2005 | Larson et al. ............ | 239/102.1 |
| 7,097,810 | B2 * | 8/2006 | Chang et al. ............. | 422/100 |
| 7,125,727 | B2 * | 10/2006 | Massaro ................. | 436/180 |
| 7,258,480 | B2 * | 8/2007 | Dunfee et al. ............ | 366/197 |
| 7,303,728 | B2 * | 12/2007 | Boillat et al. ............ | 422/100 |

(Continued)

OTHER PUBLICATIONS

European Search Report for EP 04 076 436.7 dated Oct. 20, 2004.

(Continued)

*Primary Examiner*—Brian R. Gordon
(74) *Attorney, Agent, or Firm*—McDonnell Boehnen Hulbert & Berghoff LLP

(57) ABSTRACT

A method and a micropipetting apparatus is described for dispensing a liquid volume into a vessel via pipetting needle without any contact between the needle and a liquid contained in the vessel. The method comprises forming a drop at the delivery tip of the pipetting needle, the drop being retained at the tip by adhesion forces, and ejecting the drop from the tip of the pipetting needle by focusing at the tip of the pipetting needle a mechanical excitation wave applied at an excitation point at some distance from the tip of the pipetting needle. The apparatus comprises a pipetting needle, an electromechanical transducer mechanically connected with said pipetting needle for mechanically exciting the pipetting needle with a pulse of mechanical waves that propagate through the needle, and an electrical signal generator for generating an excitation pulse signal and for applying this signal to the electromechanical transducer.

13 Claims, 13 Drawing Sheets

U.S. PATENT DOCUMENTS

2002/0150511 A1*  10/2002  Wiktor ...................... 422/100
2004/0071601 A1    4/2004  Larson et al. ............... 422/100
2005/0095723 A1*   5/2005  DiTrolio et al. ............. 436/180

OTHER PUBLICATIONS

European Search Report for EP 05 07 5977.8 dated Feb. 3, 2006.
Dual, Jürg, "Micro- and Nanomechanics," IMES, Seite 1 von 24, http://www.zfm.ethz.ch/e/res/mic/ printed Jul. 27, 2004.
Drafts, Bill, "Acoustic Wave Technology Sensors," IEEE Transactions on Microwave Theory and Techniques, vol. 49, No. 4, Apr. 2001.
Graff, K.F., "Wave Motion in Elastic Solids," Ohio State University Press, 1975, pp. 180-187 and 474-481.
Doyle, J.F., "Wave Propagation in Structures," Springer, New York, 1989, pp. 6-9.
Thesis of Leutenegger, Tobias F., "Detection of Defects in Cylindrical Structures Using a Time Reverse Numerical Simulation Method," Swiss Federal Institute of Technology, Zurich, Switzerland, No. 14833, 2002, pp. 11-43.

* cited by examiner

PIPETTING NEEDLE

APPLICATION PRIORITY INFORMATION

This application claims the benefit of European Patent Application Number EP 04076436.7 filed on May 14, 2004.

FIELD OF THE INVENTION

The invention generally concerns pipetting technology and more specifically relates to methods and devices for dispensing a liquid drop into a vessel without contact between the pipetting needle and a liquid in the vessel.

BACKGROUND

Pipetting of liquids is an important function of automatized analysis of samples examined for the purposes of medical diagnosis. Mastering of the pipetting operations is a basic condition for performing analysis which are correct, fast, cheap and ecological. There is a need for a pipetting apparatus which is able to pipette with the required accuracy liquid volumes in the nanoliter and microliter range.

Historically, dispensing of very small liquid volumes requires contact of the pipetting needle with a solid surface or with another liquid to which the dispensed volume is added. This is so because the adhesion forces which retain the small volume to be dispensed to the pipetting needle are larger than the weight of that small liquid volume. This weight alone is thus not sufficient for releasing a drop attached by adhesion forces to the tip of a pipetting needle. In prior art automatic pipetting apparatus of analyzers used for medical diagnosis a drop of a liquid to be dispensed is therefore brought into contact with and thereby delivered into another liquid, which can be a sample or a reagent. In order to avoid erroneous analysis results, it is necessary to clean the pipetting needle after each such contact with liquid in a container and this requires a lot of time.

According to prior art delivery of a liquid to be dispensed can only be achieved by contact of the tip of the pipetting needle with a liquid contained in a container which receives the dispensed liquid. In some applications it is however desirable to dispense a liquid without any contact between the tip of the pipetting needle and a liquid contained in a container that receives the dispensed liquid, since in this case cleaning of the needle would not be necessary after each dispensing operation. This is the case for example, when aliquots of a liquid sample are to be distributed to liquids contained in a plurality of containers. In this case the time for distributing the aliquots to the plurality of containers would be considerably reduced, because it would not be necessary to clean the pipetting needle after dispensing each aliquot.

FIG. 1 shows a prior art dispensing of very small aliquots of a liquid to a plurality of different vessels. As shown in FIG. 1, a pipetting needle 11 is used for taking a sample of liquid contained in a vessel 12 and for successively dispensing aliquots of that sample to different vessels 13 and 14. For each such dispensing the tip needle 11 has to contact a liquid contained in the vessel 13, 14 which receives the aliquot. For the reasons mentioned above the needle 11 has to be cleaned after each such dispensing, before dispensing an aliquot in a different vessel. FIG. 1 shows cleaning positions 15 and 16 of the pipetting needle. In FIG. 1 arrows represent the sense of motion of the pipetting needle during the above-mentioned dispensing operations.

Drops can be dispensed in a number of ways. For instance, in inkjet printers a pressure pulse is generated within a liquid and this pulse propagates towards a nozzle which closes one end of a container containing the liquid to be dispensed. Due to the reduction of the cross-section at the transition from the interior of the container to the nozzle, a small liquid volume is strongly accelerated and this allows to release through the nozzle one drop of liquid from the container. The size of a drop generated by the inkjet principle lies in a range going from 5 to 500 picoliter and depends upon properties of the liquid and the size of the nozzle. Drops generated only by the weight of the drop to be dispensed are much larger. When a pipetting needle having a cross-section with an external diameter of 10 micrometers is used for dispensing drops only by means of gravitational force (i.e. the weight of the drops) the size of each drop would be of 30 nanoliters if the liquid dispensed is an aqueous solution.

When dispensing drops by the inkjet principle, a very strong acceleration of the liquid volume in the nozzle is necessary (accelerations of up to $10^5$ g). The energy required for releasing a 500 picoliter drop is of about $10^{-8}$ Joule.

It is believed that a nozzle of the type used in inkjet printers cannot be a part of a pipetting needle of a device for analyzing samples for medical analysis, because the structure of the pipetting needle should allow the sufficient cleaning, but the presence of a nozzle in the structure of the pipetting needle would render this difficult.

Other features that a pipetting needle may fulfill are: (i) being suitable for piercing a closure of a liquid container, and (ii) having an elongated shape that is sufficiently long to penetrate to a predetermined level in a liquid container.

SUMMARY

The presently described embodiments concern a method for dispensing a liquid volume into a vessel by means of a pipetting needle and without any contact between said needle and a liquid contained in said vessel. The embodiments further concern a micropipetting apparatus for dispensing a liquid volume into a vessel by means of a pipetting needle and without any contact between said needle and a liquid contained in said vessel.

An aim of the embodiments is to provide a method and an apparatus which can enable a contact-free dispensing of liquid drops from the tip of a pipetting needle, and which in particular allow the use of a pipetting needle which can be properly cleaned by washing it with conventional washing means and which is suitable for piercing a closure of a vessel.

There are a number of advantages associated with the various embodiments. An embodiment of the method allows a contact-free dispensing of drops without including a nozzle in the structure of the pipetting needle. A thorough cleaning of the pipetting needle is therefore possible. In a further embodiment, achievement of the technical effects attained with the method, in particular the focusing of the mechanical waves at the delivery tip of the pipetting needle, does not require or depend on any specific geometrical features of the pipetting needle. This method thus makes it possible, in some embodiments, to achieve those effects using pipetting needles having various shapes and dimensions. Release of drops from a pipetting needle is achieved by use of a piezoelectric actor and does not require use of any movable part. Further, in practice, a complete system including a piezoelectric transducer and liquid contained in the pipetting needle can be simulated by means of a finite difference method (FDM) Code. Other advantages may stem from the embodiments as well. As such, these advantages should not be seen as limiting the claimed subject matter.

BRIEF DESCRIPTION OF THE DRAWINGS

Several embodiments will now be described with reference to the accompanying drawings. These embodiments are set forth to aid the understanding of the invention, but are not to be construed as limiting.

DETAILED DESCRIPTION OF AN EMBODIMENT

A method is described hereinafter with reference to FIGS. 2 to 12. This method is suitable for dispensing a liquid volume into a vessel by means of a pipetting needle and without any contact between said needle and a liquid contained in said vessel.

Figure 1:
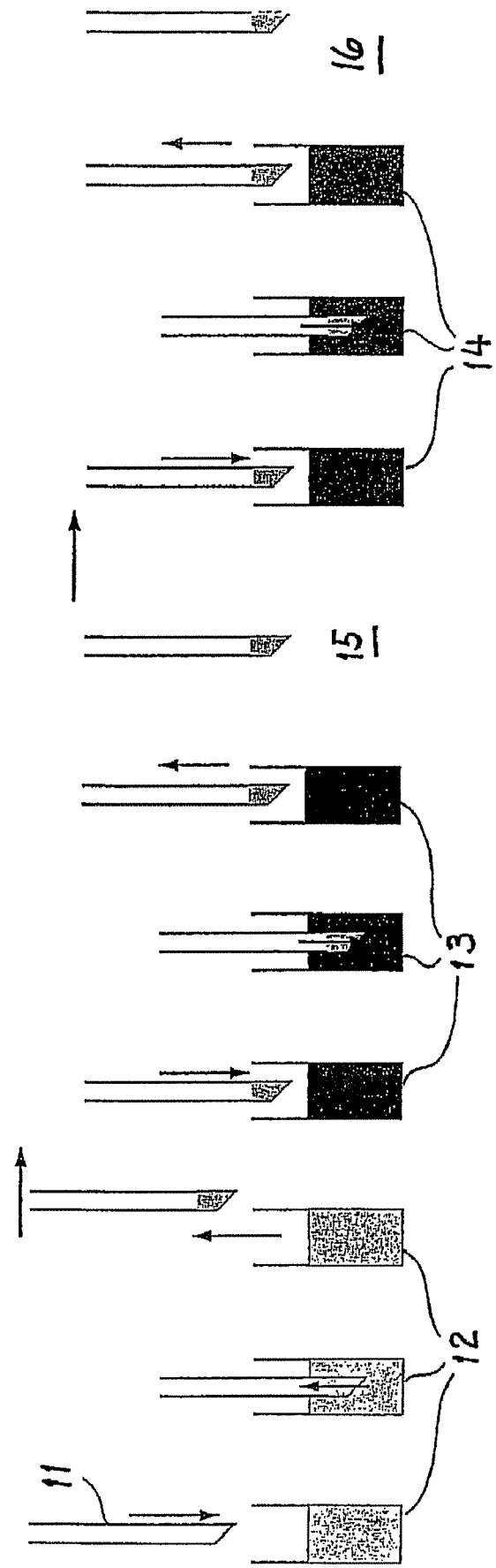
FIG. 1 shows schematically a prior art method for dispensing aliquots of a liquid sample taken with a pipetting needle from a vessel to a plurality of vessels.
Figure 2:
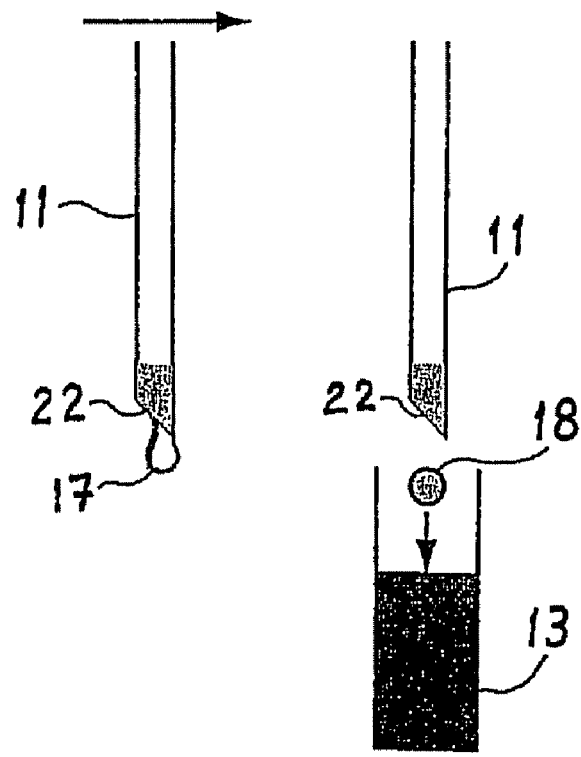
FIG. 2 shows schematically the principle of a method for dispensing aliquots of a liquid sample taken with a pipetting needle from a vessel to another vessel.

As shown in FIG. 2 a volume of liquid 17 corresponding to the volume of a drop to be dispensed is formed at the tip 22 of a pipetting needle 11 by exerting pressure on the liquid contained in the interior of the pipetting needle. Adhesion forces retain the drop so formed attached to the tip 22 of the pipetting needle 11. By performing a method described hereinafter the volume 17 is ejected from the tip of needle 11 as a drop 18 which is delivered to and thereby added to a liquid contained in a vessel 13. It should be noted that drop 18 is delivered without any contact between needle 11 and a liquid contained in vessel 13.

Figure 3:
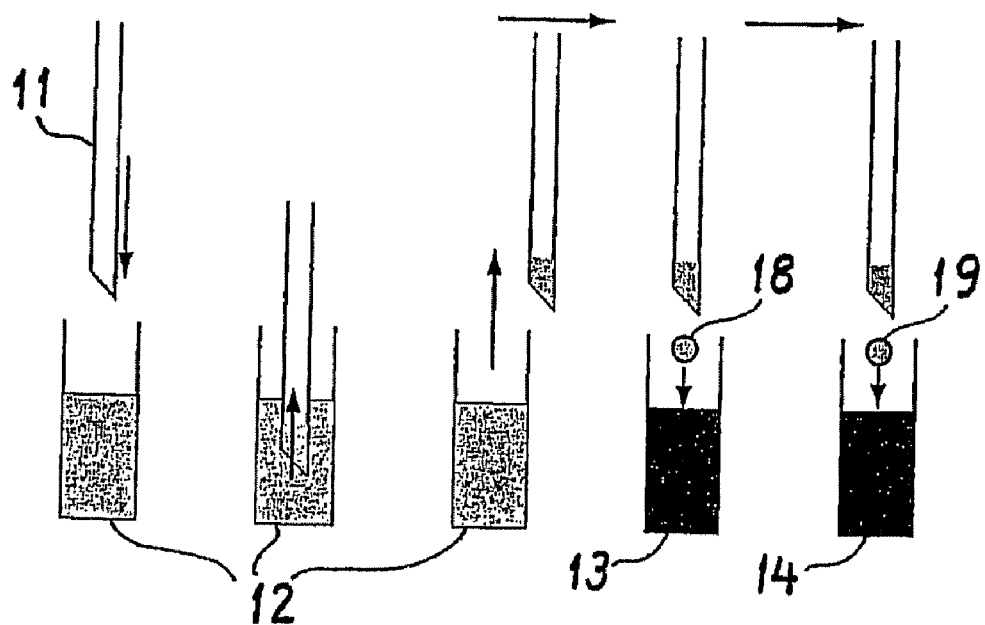
FIG. 3 shows schematically successive dispensing of drops to different vessels by the method represented in FIG. 2.
Figure 4:
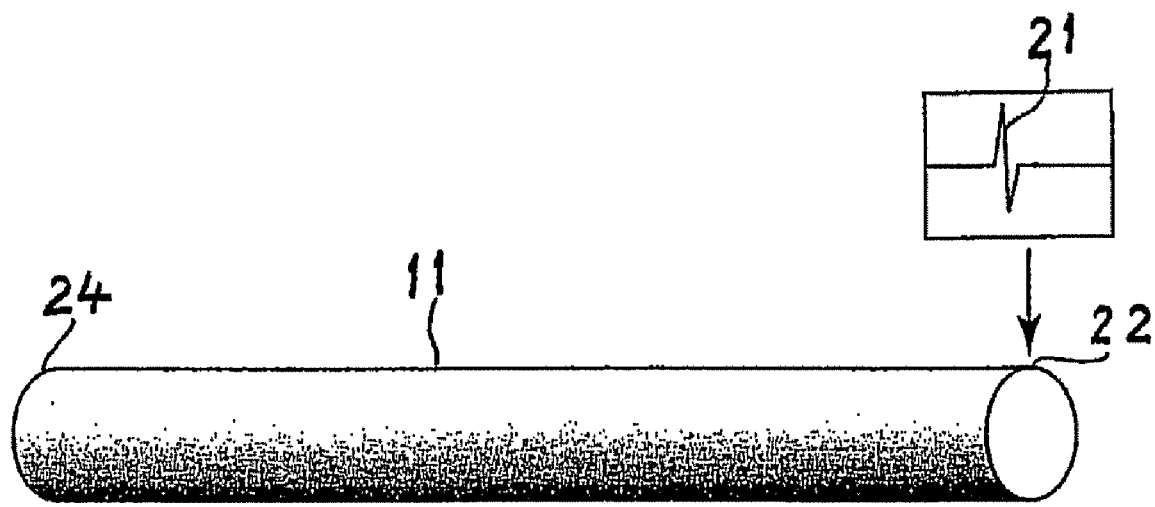
FIG. 4 shows schematically a simulation step wherein a desired focused mechanical pulse is applied as excitation pulse at a first location of a pipetting needle.

FIG. 3 illustrates a successive dispensing of drops 18, 19 to different vessels 13, 14 respectively, by the method represented in FIG. 2.

The embodiment makes use of the fact that the tubular wall of the pipetting needle 11 is a dispersive medium for the transmission of mechanical waves. Due to the dispersion characteristics of the pipetting needle, a mechanical wave which is applied at a first point (excitation point) of the pipetting needle and propagates through the tubular wall of the needle travels towards the tip of the needle at a speed which depends on the frequency of that wave.

Figure 18:
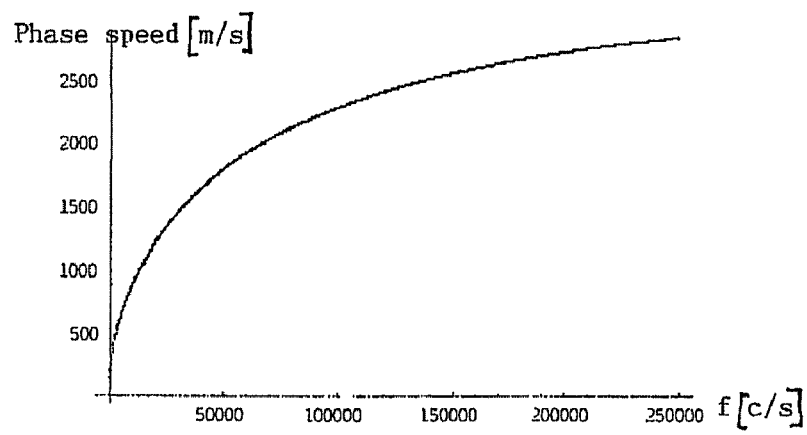
FIG. 18 shows the dispersion characteristics of a Timoshenko beam.

The physical facts which cause the above mentioned dispersion properties of the pipetting needle can be explained as follows:

In the case of a simple beam (e.g. a steel beam having a radius of 0.005 m) that obeys Timoshenko Beam theory (see Graff, K. F., Wave Motion in Elastic Solids, Ohio State University Press, 1975), due to the dispersion characteristics of such a beam the phase speed of a mechanical wave that propagates through the beam is a function of the frequency of the mechanical wave. FIG. 18 shows the dispersion characteristics of the above-mentioned Timoshenko beam, i.e. how the phase speed varies as a function of the frequency in such a case. According to FIG. 18 mechanical waves which have higher frequencies propagate through the beam with higher phase speeds and have also higher group velocities than mechanical waves which have lower frequencies. This means that mechanical waves which have higher frequencies travel faster than mechanical waves which have lower frequencies.

Figure 19:
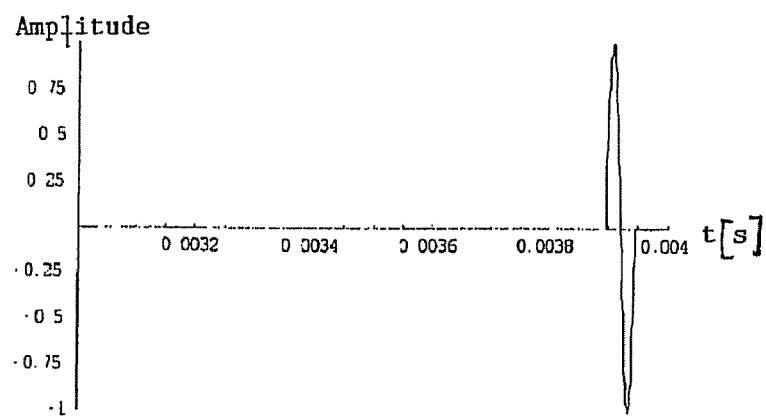
FIG. 19 represents a desired transverse displacement pulse at a given point of a Timoshenko beam.

FIG. 19 represents a transverse displacement pulse corresponding to one period of a sine signal with an Amplitude=1 at a location x=1 m, i.e. at a distance of 1 m from the point of the beam where a mechanical excitation is applied.

Figure 20:
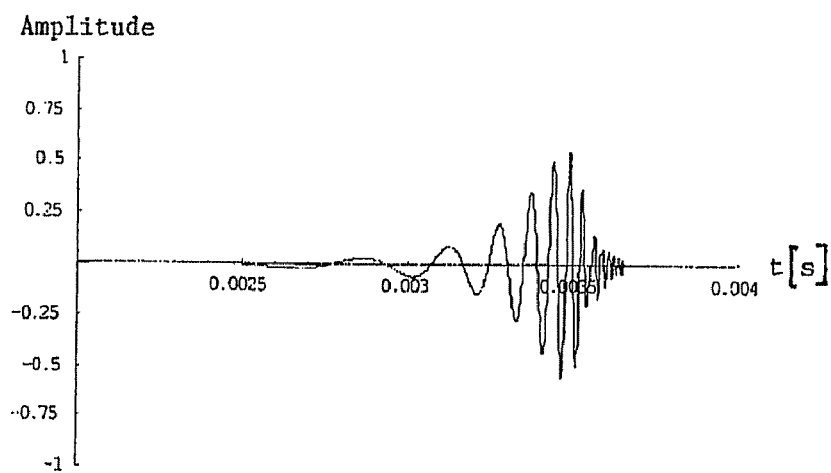
FIG. 20 represents a mechanical excitation pulse applied at an excitation point of a Timoshenko beam in order to obtain the transverse displacement pulse shown by FIG. 19.

In order to obtain the transverse displacement pulse shown by FIG. 19 it is necessary to apply at the excitation point of the beam a mechanical excitation which corresponds to the signal represented by FIG. 20. Such a signal is computed using the dispersion characteristics shown by FIG. 18 and in the frequency space using well known methods based on the Fourier Transform described e.g. by Doyle, J. F., Wave Propagation in Structures, Springer, N.Y., 1989.

FIG. 20 shows that the low frequency components of the excitation signal have to be sent off first, because their wave speed is smaller. This is the basic principle used according to the embodiment for focusing a pulse using the dispersion characteristics of a mechanical structure: a relatively long pulse is transformed by the dispersion characteristics of the beam into a short pulse that can be used e.g. for releasing a drop as proposed by the instant embodiment.

If a tube is used instead of a beam as medium for transmitting a mechanical wave, the dispersion characteristics necessary for computing the excitation signal can be taken from any book of wave propagation, e.g. Graff, K. F., Wave Motion in Elastic Solids, Ohio State University Press, 1975. In a tube there are several propagation modes and each mode has its own dispersion characteristics. This property can be used in addition for obtaining the desired focusing effect. An additional focusing effect is obtainable by effecting suitable time delays of pulses of the various modes with respect to each other and thereby obtaining an overlap of pulses corresponding to the various modes at a desired location.

According to a preferred embodiment of the method pulses of several modes of propagation having each their individual dispersion characteristics are focused and superimposed at the tip of the pipetting needle 11. This is achieved for instance by effecting suitable time delays of pulses of the various modes with respect to each other and thereby obtaining an overlap of pulses corresponding to the various modes and a focusing of the energy of those pulses at the tip of the pipetting needle 11.

The portion of the pipetting needle 11 used according to the embodiment for the above mentioned transmission of mechanical waves is shown in FIGS. 4 to 9. This portion has the shape of a capillary tube.

According to the embodiment a suitable composite mechanical excitation pulse is applied at a point 24 of the pipetting needle which lies at some distance from the needle delivery tip 22 from which the drops are ejected. The latter excitation pulse and the mechanical system comprising the needle 11, the liquid in the needle and the means for generating the excitation pulse, e.g. a piezoelectric transducer connected to the needle, are so configured that the excitation pulse has frequency components which arrive simultaneously to the drop delivery tip 22 of the needle and thereby provide a maximum of mechanical energy at that tip. In other words the latter configuration is such that transmission of the excitation pulse by the mechanical system mentioned above focuses the mechanical wave at the tip 22 of the pipetting needle and reflection of the focused wave at that tip causes ejection of a drop which was held there by adhesion forces.

According to the embodiment a drop 17 is formed at the delivery tip 22 of the pipetting needle 11 by pressing a predetermined liquid volume out of the needle and thereby forming a liquid meniscus at the delivery tip 22 of the pipetting needle. After that the above mentioned transmission/propagation 27 of mechanical waves through the needle 11 can take place, e.g. in one of the following ways:

1) A mechanical excitation pulse is applied to the needle at point 24. This pulse causes displacements in the tubular wall of the needle 11 mainly in axial direction and is focused at the delivery tip 22 of the needle. The reflection of this pulse at the delivery tip 22 of the pipetting needle releases drop 17 from that tip.

2) A mechanical excitation pulse is applied to the needle 11. This pulse causes displacements in the tubular wall of the needle mainly in radial direction. Due to mechanical coupling of the tubular wall of the needle 11 and liquid contained in the needle, liquid within the needle is also displaced and accelerated towards the delivery tip 22 of the needle by the propagation of the excitation pulse. This displacement of fluid and the focusing and reflection of the excitation pulse at the delivery tip 22 of the pipetting needle releases drop 17 from that tip.

The above described method for dispensing a liquid thus essentially comprises (a) forming a drop 17 at the delivery tip 22 of a pipetting needle 11, said drop being retained at the tip by adhesion forces, and (b) ejecting the drop 17 from the tip 22 by focusing a mechanical wave at the tip 22 of the pipetting needle 11.

In a preferred embodiment the ejection of the drop is achieved by mechanically exciting the needle by means of an excitation pulse having a composition that focuses a pulsed wave at the tip of said pipetting needle. A superposition of a focused incident wave with a reflected wave at the delivery tip of the pipetting needle causes ejection of the drop from the tip. As described hereinafter a suitable composition of the excitation pulse is obtained by a simulation process.

Embodiment of a Method for Generating an Excitation Pulse

In order to generate an excitation pulse which has a composition or structure suitable for performing a method according to the embodiment, the wave propagation of a desired focused pulse in a system comprising a needle filled with a liquid and a piezoelectric actuator mechanically connected with the needle is simulated by means of finite difference method (FDM). After that an excitation pulse with a suitable structure for obtaining the desired focused pulse is calculated by a time reversal method.

In order to simulate the above mentioned wave propagation a FDM code is written for the case of an axial symmetric tube, filled with a liquid and mechanically connected to a piezoelectric transducer. The latter FDM code is based on a code described in the publication: Thesis of Tobias F. Leutenegger entitled "Detection of defects in cylindrical structures using a time reverse numerical simulation method", thesis submitted at the Swiss Federal Institute of Technology, Zurich (ETH Zürich), Switzerland, No. 14833, 2002.

The FDM code is programmed with second order central differences, a so called staggered grid being used for discretization in space and time. The liquid is modeled as an acoustical fluid. In this way the behavior of the complete system can be simulated. By means of the FDM code the excitation pulses necessary for the desired energy focusing are computed making use of a time reversal method. The principle of this method is described as follows with reference to FIGS. 4 to 12, wherein a portion of pipetting needle is shown, and this portion has the shape of a capillary tube:

A real experiment with the pipetting needle is described by/simulated with a FDM code. The spot 24, where the mechanical excitation pulse is applied to the needle, and the spot 22, where the mechanical pulses should be focused, are defined.

In the FDM code a desired focused pulse 21 is applied as excitation pulse at the spot 22, where the mechanical pulses should be focused in the real experiment.

The propagation 23 of the mechanical wave is simulated over a time interval which extends until the excitation pulse passes through the spot 24, where the mechanical excitation pulse is applied to the needle in the real experiment.

The displacements in all directions are recorded as a signal 25 over a time interval at the spot 24, where the mechanical excitation pulse is applied to the needle in the real experiment.

Figure 7:
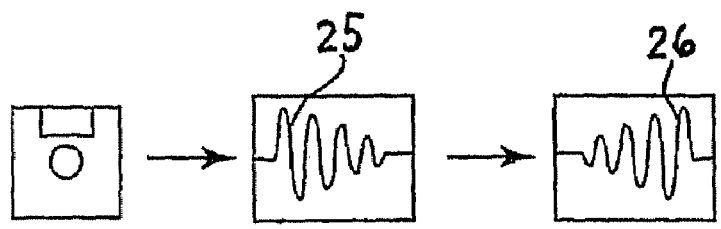
FIG. 7 shows schematically time inversion of the recorded signal for generating an excitation pulse.
Figure 8:
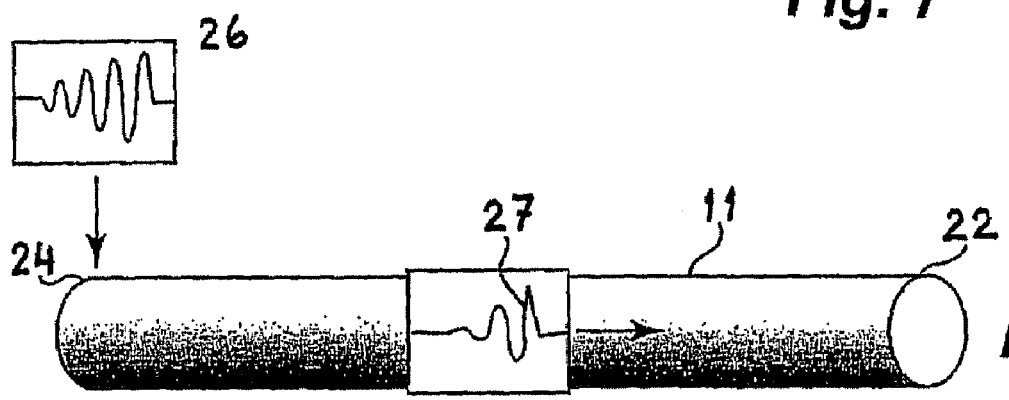
FIG. 8 shows schematically application of the excitation pulse and propagation of that pulse.
Figure 9:
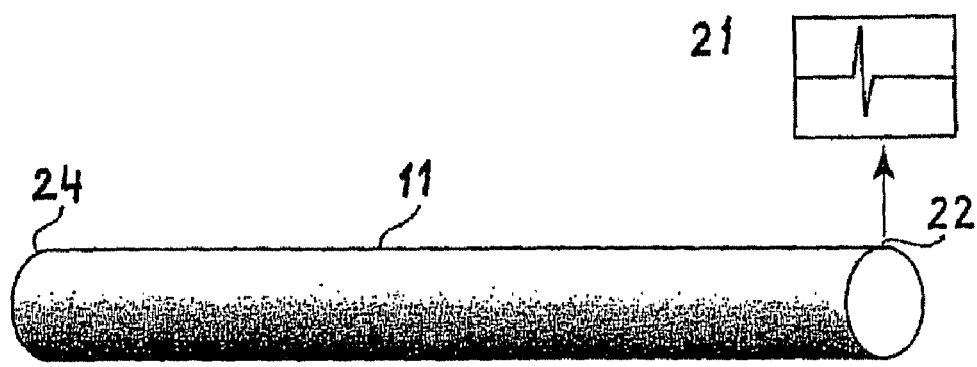
FIG. 9 shows schematically a desired focused mechanical pulse as a result of the propagation represented in FIG. 8.

The recorded signal 25 is reversed in time for generating a signal 26 which is the excitation signal that has to be applied at spot 24, where the mechanical excitation pulse is applied to the needle in the real experiment, in order to obtain a desired focused pulse 21 at the spot 22, where the mechanical pulses should be focused in the real experiment (see FIGS. 7 to 9).

The result of the above mentioned calculation is the electrical signal 26 to be applied to the piezoelectric transducer. This signal is generated by a function generator. A piezoelectric tube with electrodes on its major surfaces (radial electric field) and radial polarization generates mainly radial displacements. A piezoelectric tube with electrodes on its major surfaces (radial electric field) and axial polarization generates mainly axial displacements. Generation of the desired displacements in the pipetting needle can thus be obtained by election of a suitable piezoelectric transducer.

Figure 17:
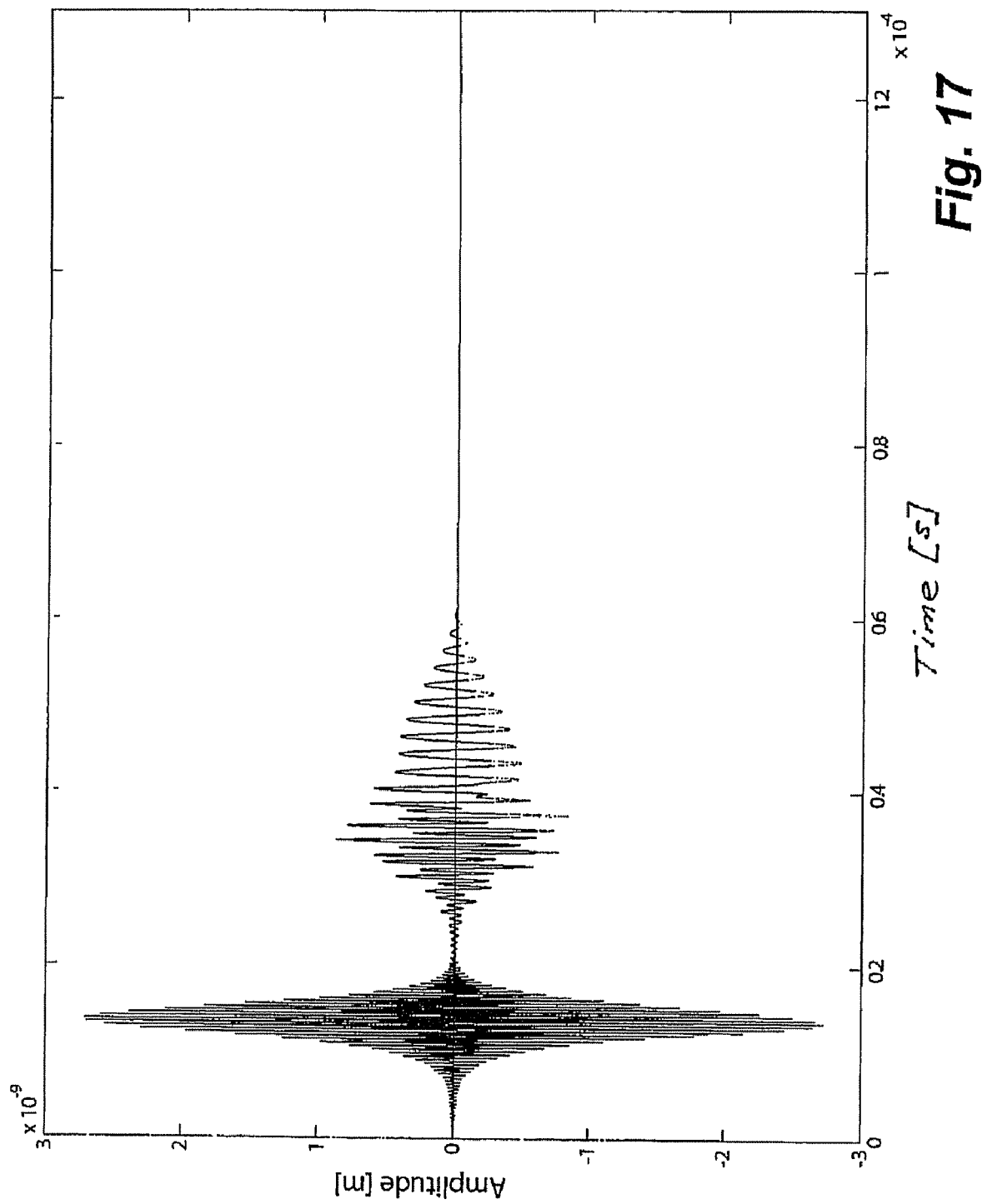
FIG. 17 shows an example of a wave shape of an excitation pulse signal.

FIG. 17 shows an example of the wave shape of excitation pulse signal 26 obtained as described above by simulation of the wave propagation in the tubular body of the needle and by time reversal of the signal recorded in that simulation. The obtention of the latter excitation pulse signal 26 thus takes into account the complete wave propagation behavior of that tubular body, all wave propagation modes in the frequency range used and their frequency dependent propagation speeds.

A method for generating an excitation pulse signal 26 that has a composition suitable for focusing the energy applied by that pulse to the pipetting needle is described as follows. To simplify the description and make it easier to understand the method is described for the simplified case of a pipetting needle which has the shape of simple empty tube, which does not contain any liquid and which is not mechanically coupled with any electromechanical transducer. A FDM code of the above mentioned case is written for this case and is used for the simulation.

Figure 10:
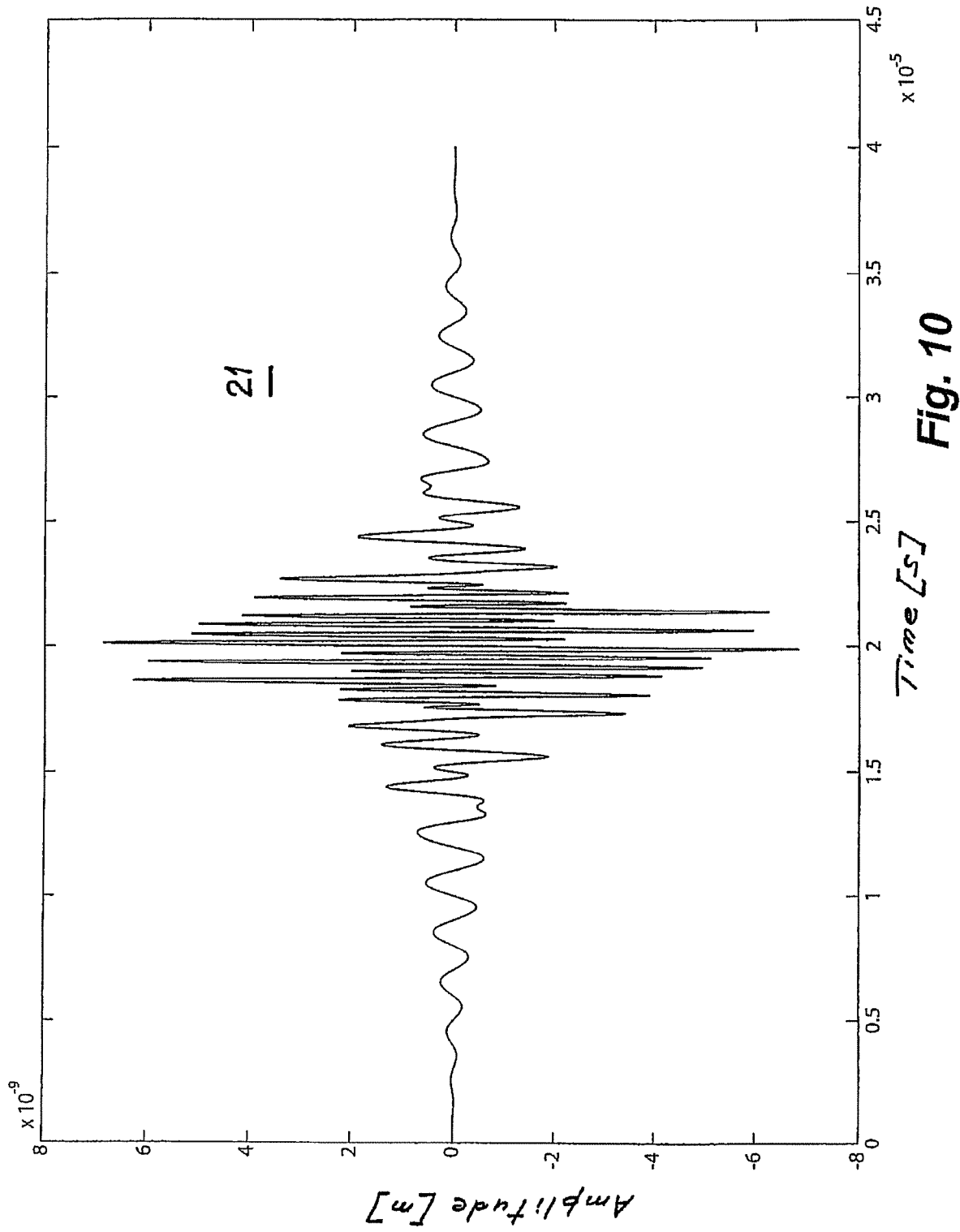
FIG. 10 shows an example of a wave shape of a focused mechanical pulse in a simplified structure not taking into account any liquid contained in needle and without any electromechanical transducer mechanically connected with needle. Such a pulse is used in a simulation of the type represented in FIG. 4.
Figure 11:
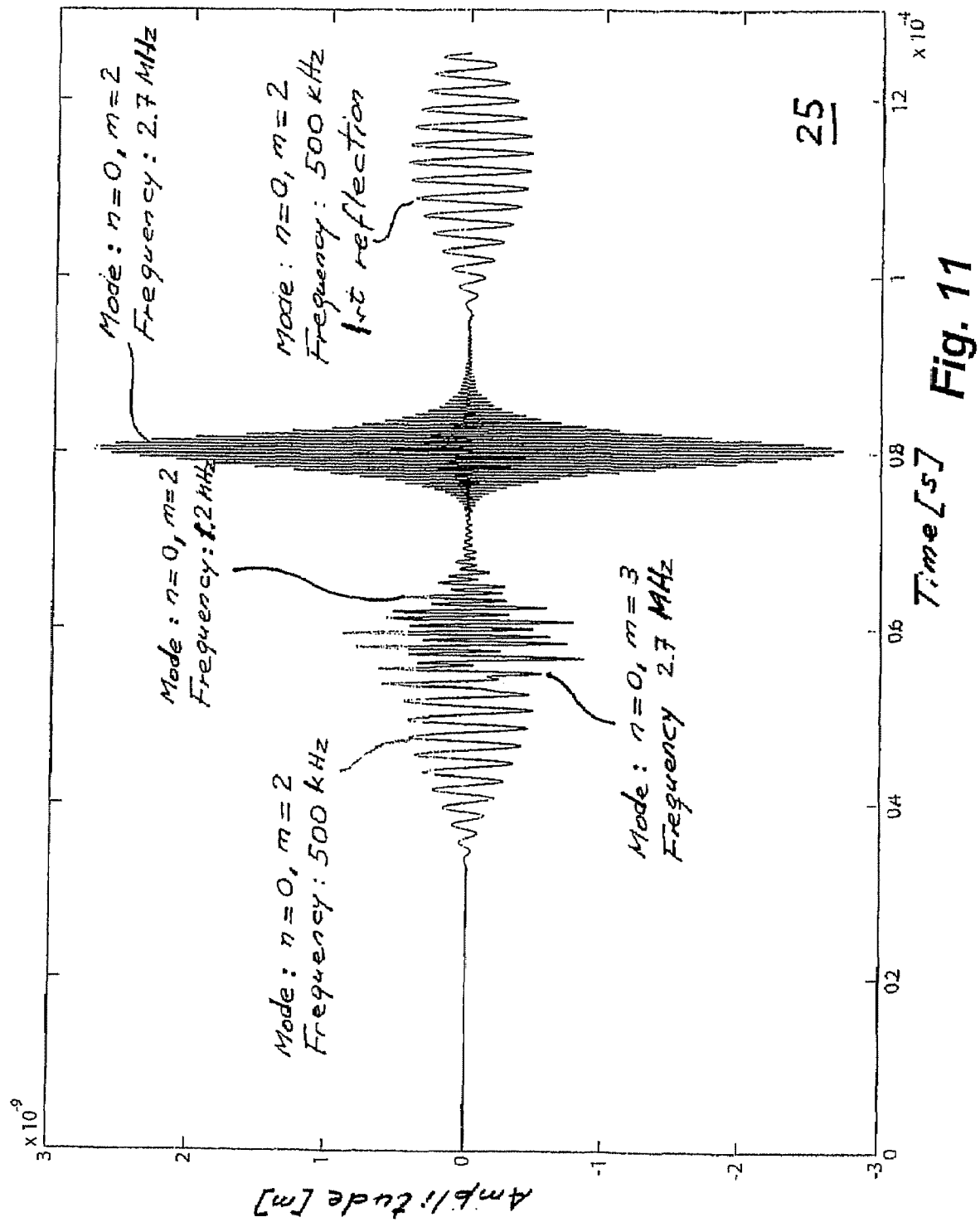
FIG. 11 shows an example of a wave shape of a signal which is recorded at a point on a pipetting needle when a mechanical pulse is applied in a simulation step under the conditions mentioned in the above brief description of FIG. 10.

Three Hanning pulses comprising each five periods of their central frequencies of 0.5 MHz, 1.2 MHz and 2.7 MHz are symmetrically superposed in order to form a desired pulse 21 shown by FIG. 10 which should be the pulse resulting from focusing the excitation pulse applied to the needle. In the simulation this desired pulse 21 is applied at the spot 22, where the mechanical pulses should be focused in the real experiment, and a signal 25 shown by FIG. 11 is recorded at the spot 24, where the mechanical excitation pulse is applied to the needle in the real experiment. Time reversal of recorded signal 25 and selection of a portion of this signal with a suitable time window provides the excitation pulse 26. The time window is so chosen that only the first arriving pulses are considered, but not those already reflected. An excitation pulse 26 obtained in the latter way is applied at spot 24 of the needle and this provides the desired focused pulse 21 shown in FIG. 12.

Figure 12:
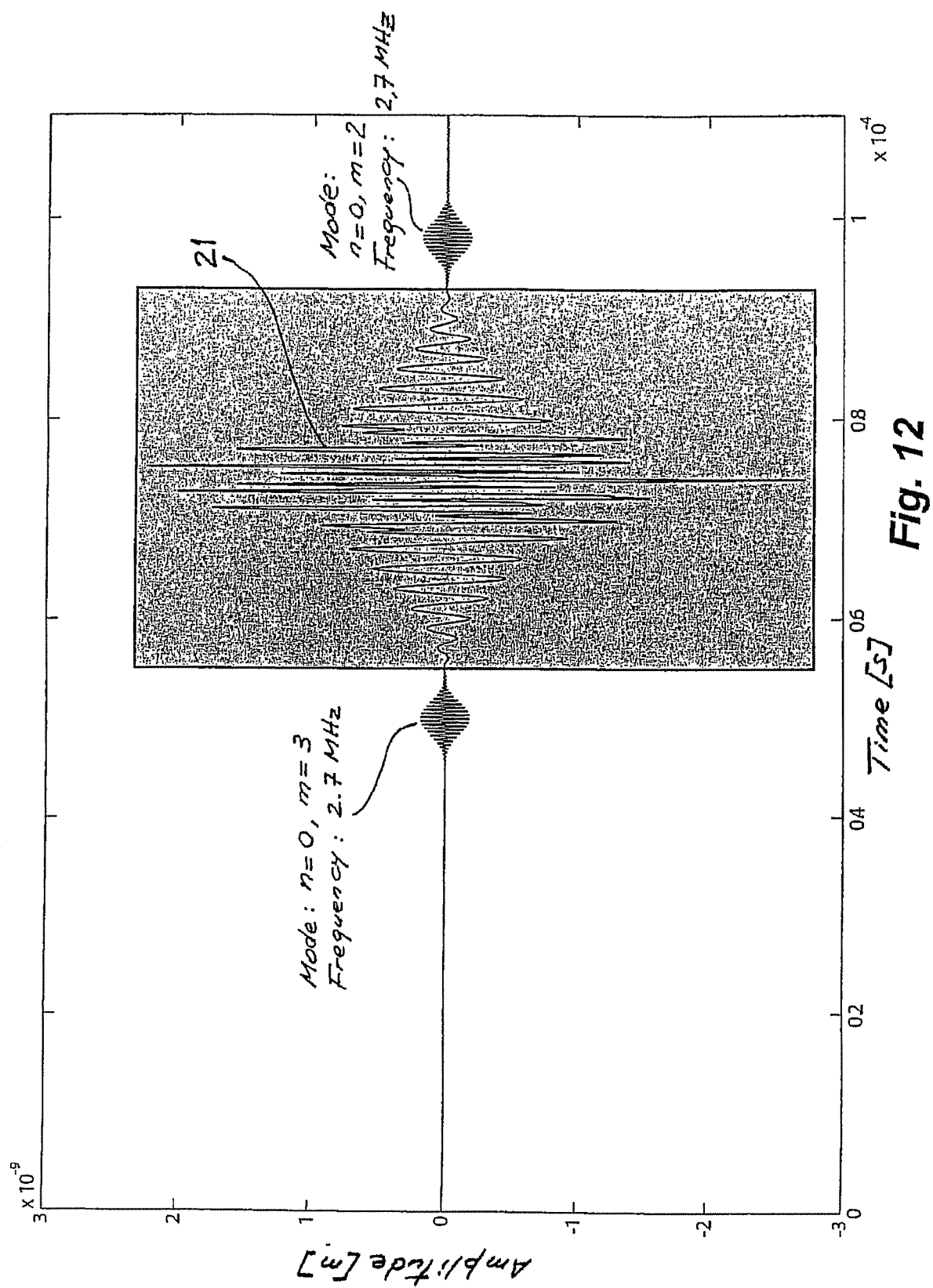
FIG. 12 shows an example of a wave shape of a focused mechanical pulse when a signal applied to the needle is obtained from a signal shown in FIG. 11 by the method step represented in FIG. 7 and under the conditions mentioned in the above description of FIG. 10.

The meaning of n and m in the labels of FIGS. 11 and 12 is as follows:

n is the azimuthal wave number and describes wave modes with regard to their azimuthal characteristic; n=0 means that the wave mode has an axial symmetry; n=1 means that the displacements have one maximum and one minimum over the circumference; n=2 means that the displacements have two maxima and two minima over the circumference.

Modes of a given wave number n are numbered in the order of their appearance with m=1, m=2, etc.

In the case of a capillary tube (e.g. the portion of a pipetting needle shown by FIGS. 4 to 9) operating at low frequencies, there is only a first mode with n=0, m=1 and a second mode with n=0 and m=2. The first mode is a torsional mode. At sufficiently low frequencies the second mode is a longitudinal mode. A third mode with n=0, m=3 arises at a frequency of 2.7 MHz.

Displacements in radial and axial direction at the complete front surface of the left end of the capillary are recorded. In FIG. 11 only axial displacements at the inner diameter of the left end of the capillary are represented.

In order to obtain a most suitable excitation signal, it would be advantageous to record displacements over the entire front surface of the left end of the capillary, but recording of displacements at a few points of that surface would suffice.

Figure 5:
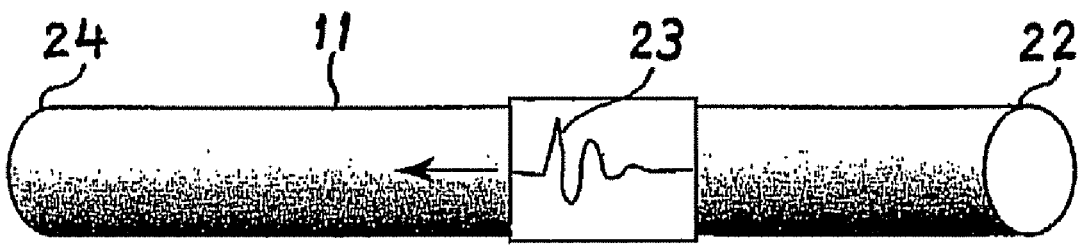
FIG. 5 shows schematically a further simulation step corresponding to the propagation of the mechanical pulse towards a desired excitation point in a real experiment.
Figure 6:
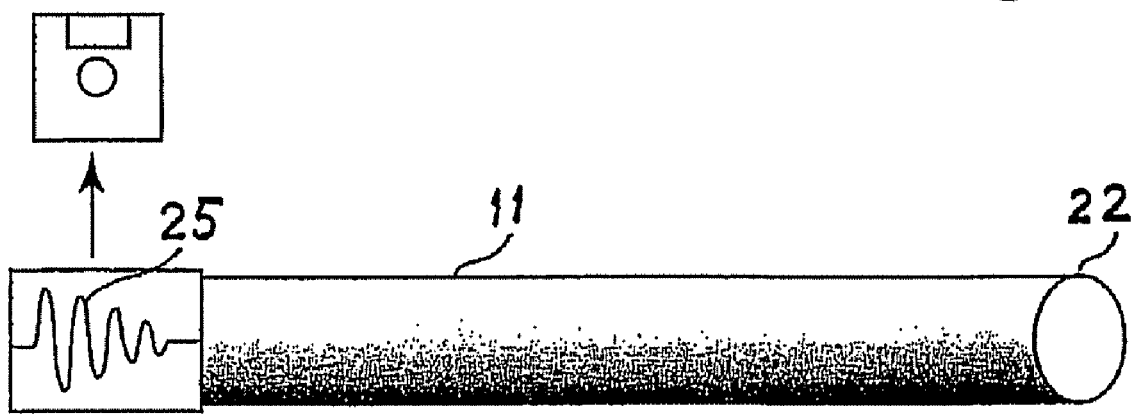
FIG. 6 shows schematically a further simulation step wherein a signal is recorded which corresponds to a mechanical pulse which reaches a second location of a pipetting needle as a result of the propagation.

FIG. 11 shows four pulses of different modes which reach spot 24 in FIG. 5 and which are the result of applying a pulse 21 at spot 22 in FIG. 5. The latter four pulses have different group velocities. Therefore, as shown by FIG. 11 these pulses reach the front surface of the left end of the capillary at different points of time. The latest pulse which reaches the latter front surface is already reflected once by the left and once by the right end of the capillary tube. This pulse should not be taken into consideration when forming the excitation pulse on the basis of the pulses shown by FIG. 11. Therefore, the time window used for forming this pulse should extend from t=0 s to about t=0.9 $10^{-4}$ s. Reversal in time of the portion of the pulses shown in FIG. 11 which are within the latter window provide an excitation pulse 26 (shown in FIG. 8) propagation 27 of which results in a pulse 21 at spot 22 in FIG. 9. In the generation of excitation pulse 26 it is important to take into account both the axial and the radial displacements obtained by simulation at the front surface of the left end of the capillary. In the attached drawings only the axial displacements are represented.

The above mentioned excitation pulse 26 consists of four pulses. FIG. 12 shows six pulses that arise at the right end 22 of the capillary tube when a mechanical excitation corresponding to excitation pulse 26 is applied at spot 24. The latter six pulses result from the four pulses of the excitation pulse 26, because above 2 MHz there are 2 propagation modes.

Four of the above mentioned six pulses form focused pulse 21 shown in the gray area of FIG. 12. Two other modes outside of this gray area are also represented in FIG. 12. These two modes, which are not desirable, but are also generated by the excitation with pulse 26, reach the right end 22 of the capillary tube at other points of time. The latter modes do not interfere with the release of a drop from the tip of the pipetting needle, because they lie outside of the time window of the desired pulse 21 which is used for releasing the drop.

The method just described above is just a simplified example of a method for focusing mechanical pulses. For the purpose of releasing drops from the delivery tip of a pipetting needle not only the behavior of a capillary tube (pipetting needle), but also the behavior of a piezoelectric transducer used for applying the mechanical pulses is simulated. Simulation of the behavior of a liquid in the interior of the needle is less important than simulation of the behavior of the capillary tube and the piezoelectric transducer, because the liquid in the needle has less influence on the process for releasing a drop by the above described method.

A suitable FDM code of the above mentioned kind is also available for performing a simulation of the behavior of the capillary tube and the piezoelectric transducer for the propagation of a mechanical pulse applied by the transducer to the capillary tube. If the simulation includes simulation of the behavior of the piezoelectric transducer, a voltage would be recorded that corresponds to the displacements shown in FIG. 11.

The above described method for generating an excitation pulse suitable for performing the above mentioned dispensing method and in particular for exciting an electromechanical transducer in a micropipetting apparatus of the kind described hereinafter essentially comprises:

(a) simulating by means of a finite difference method propagation of a mechanical pulse through the wall of a portion of a pipetting needle that has the shape of a capillary tube, said pulse being applied in the simulation at the spot where in the real experiment a focused pulse is to be generated for thereby ejecting a drop formed at the delivery tip of the needle and attached thereto by adhesion forces, (b) recording an electrical pulse signal which corresponds to mechanical pulses which in the simulation arise at the spot where the mechanical excitation pulse is to be applied to said pipetting needle in reality, and (c) calculating an excitation pulse signal to be applied in reality to said piezoelectric transducer, the latter excitation pulse signal being calculated by time reversal of said recorded signal obtained by step (b).

First Embodiment of an Apparatus for Contact-Free Dispensing of a Liquid

A first embodiment of a micropipetting apparatus is described hereinafter with reference to FIGS. 13 and 14. This micropipetting apparatus is suitable for dispensing a liquid volume into a vessel by means of a pipetting needle and without any contact between said needle and a liquid contained in said vessel.

Figure 13:
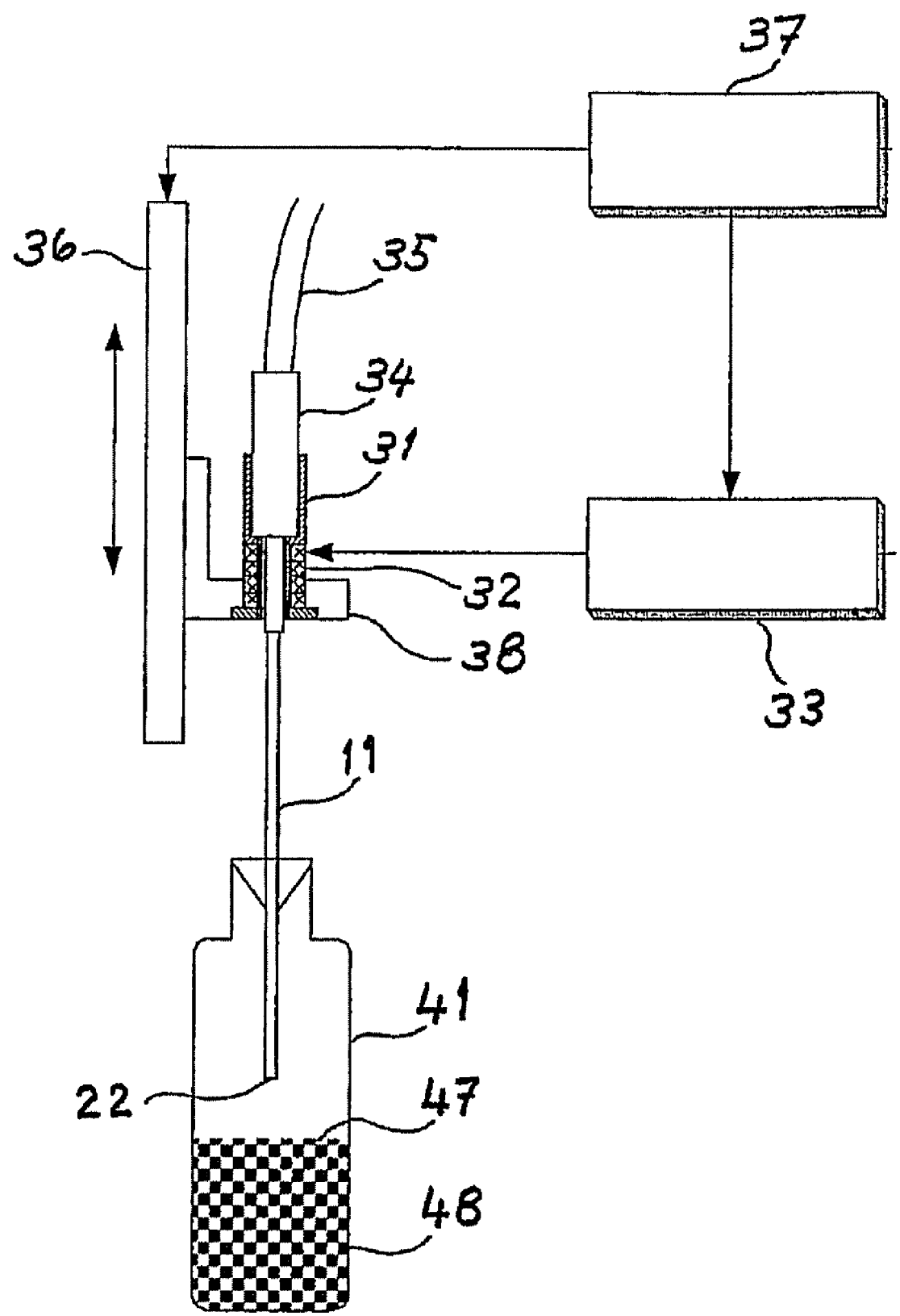
FIG. 13 shows a block diagram of the structure of an embodiment of a micropipetting apparatus.

As shown by FIG. 13 a micropipetting apparatus comprises a pipetting needle 11, a needle holder 31, an electromechanical transducer 32, a generator 33 for generating electrical signals, a connecting piece 34 which fluidically connects needle 11 with a conduit 35 which connects needle 11 with a source of positive or negative pressure, a transport system 36 for transporting needle holder 31 and a control unit 37 for controlling the operation of the entire system.

Needle 11 has a substantially constant cross-section over the portion thereof that ends in a delivery tip 22 and that portion extends over more than one half of the total length of needle 11.

Electromechanical transducer 32 is e.g. a piezoelectric transducer mechanically connected pipetting needle 11. This piezoelectric transducer comprises one or more piezoelectric elements.

Transport system 36 comprises an arm 38 which carries needle holder 31.

FIG. 13 also shows a vessel 41 containing a liquid 48 which has a free surface 47.

Figure 14:
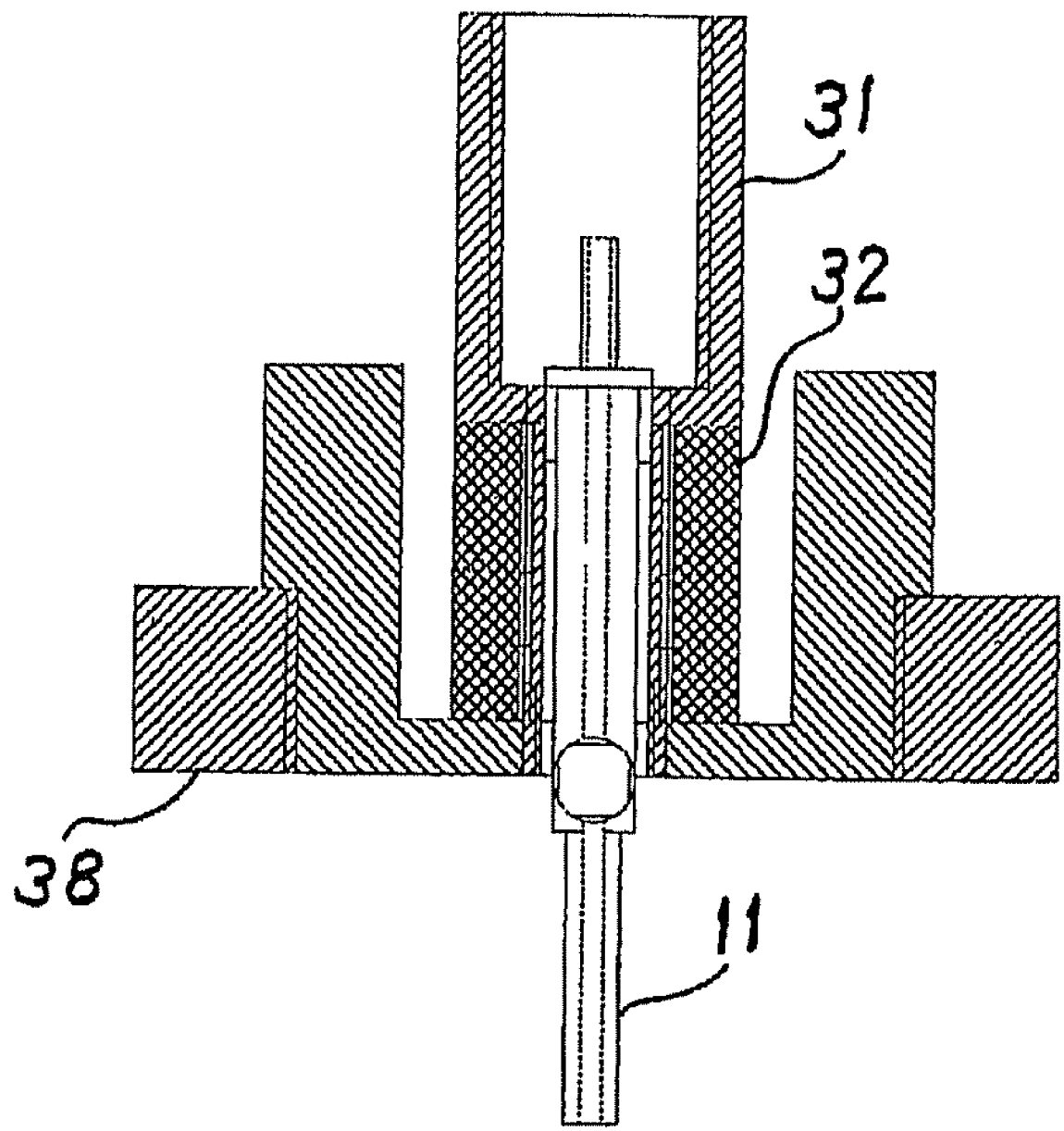
FIG. 14 shows an enlarged view of a portion of the block diagram shown by FIG. 13.

FIG. 14 shows a cross-sectional view of arm 38, needle holder 31, electromechanical transducer 32 and of a portion of needle 11.

Signal generator 33 generates an excitation pulse signal and applies this signal to piezoelectric transducer 32 for mechanically exciting pipetting needle 11 at an excitation point 24 with an excitation pulse 26 that propagates through needle 11 and is focused at the end tip 22 thereof (as shown in FIGS. 8 and 9). The latter mechanical excitation thereby causes release of a drop from tip 22 of needle 11.

In a preferred embodiment the composition of the excitation pulse 26 is adapted to the length and the wave propagation characteristics of the portion of needle 11 that has a substantially constant cross-section.

In a preferred embodiment, the piezoelectric element is radially polarized. In another preferred embodiment, the piezoelectric element is axially polarized.

In a preferred embodiment, the composition of excitation pulse signal 26 applied to piezoelectric transducer 32 is such that it causes a mainly radial displacement of liquid within said needle. In another preferred embodiment, the composition of excitation pulse signal applied to piezoelectric transducer 32 is such that it causes a mainly axial displacement of liquid within said needle.

In all above described embodiments of the micropipetting apparatus described with reference to FIGS. 13 and 14, the excitation signal 26 applied at the excitation point 24 of needle 11 is generated by a method as described above with reference to FIGS. 4-12.

EXAMPLES of PIPETTING NEEDLES USED in the ABOVE DESCRIBED APPARATUSES

Figure 15:
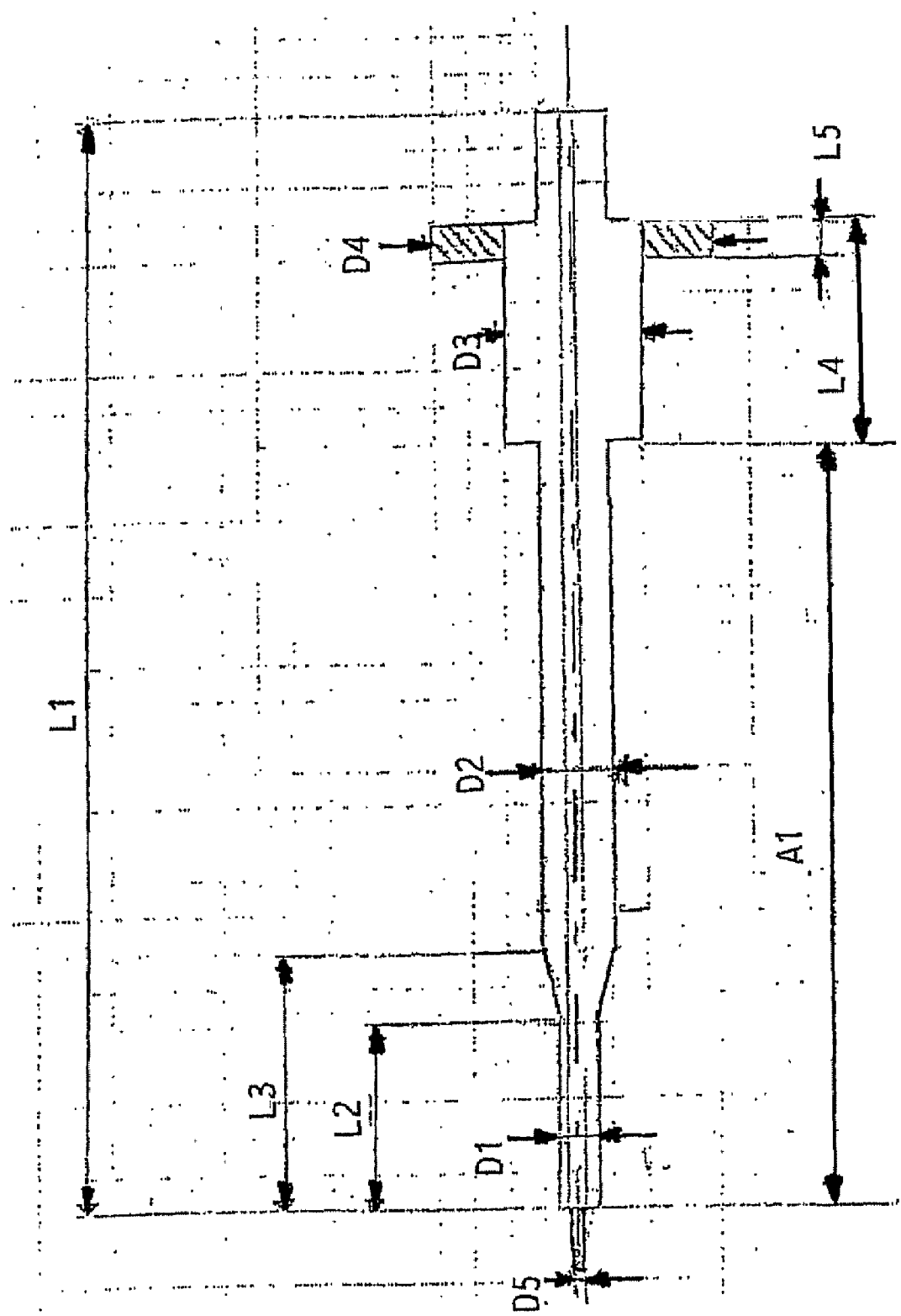
FIG. 15 shows schematically the shape and dimensions of an embodiment of a pipetting needle.

The dimensions of the pipetting needle shown in FIG. 15 are as follows:

| Dimension | Size in millimeter |
|---|---|
| A1 | 69 |
| L1 | 86 |
| L2 | 5 |
| L3 | 9 |
| D1 | 0.9 |
| D2 | 1.5 |
| D3 | 3 |
| D4 | 5 |
| L4 | 13.5 |
| L5 | 0.5 |
| D5 | 0.6 |

Figure 16:
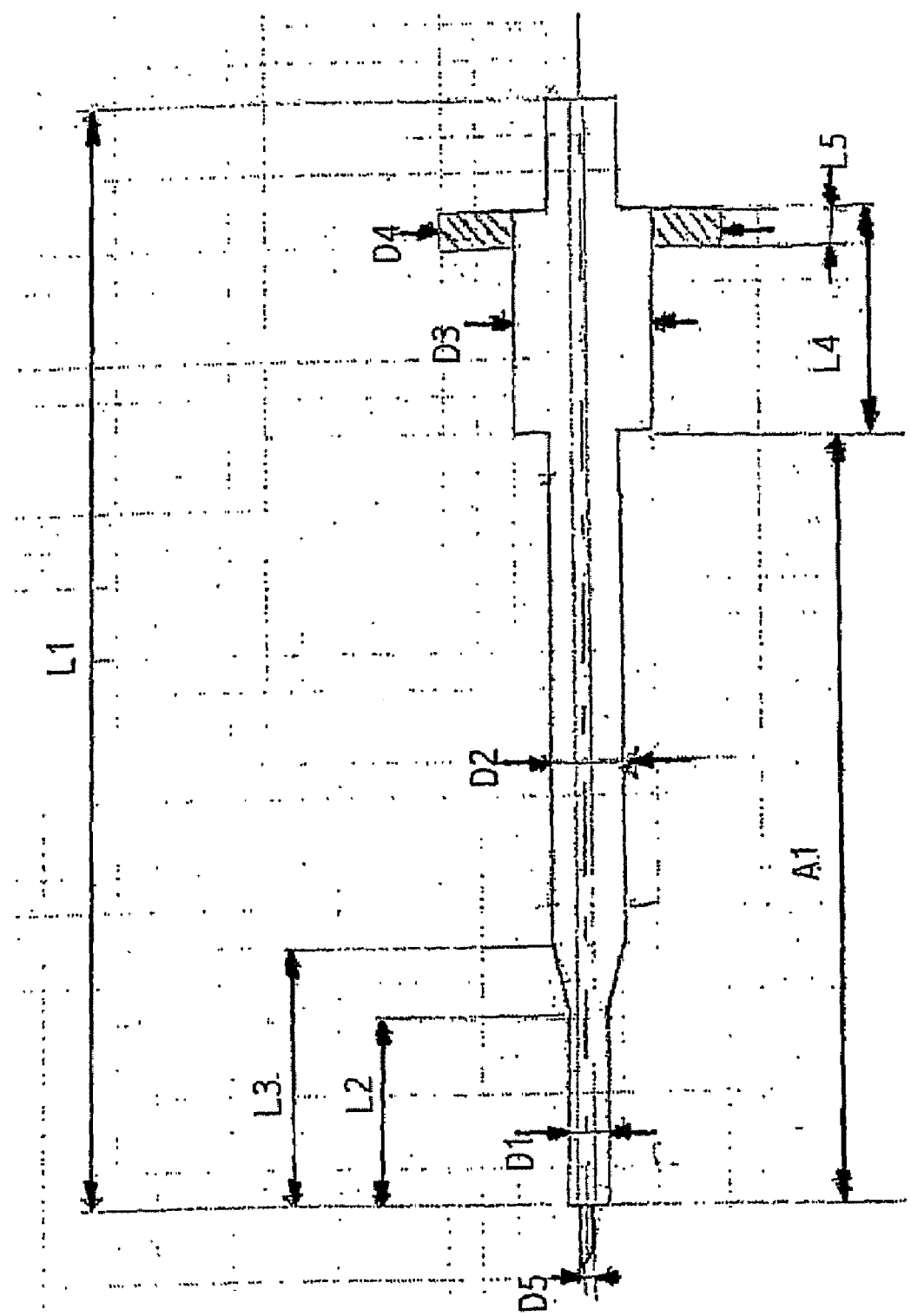
FIG. 16 shows schematically the shape and dimensions of a second embodiment of a pipetting needle.

In the embodiment of pipetting needle 11 shown in FIG. 15 the tip 22 of needle 11 has the cylindrical shape shown and that tip is shown to have a diameter D5. Another embodiment of the pipetting needle shown in FIG. 16 has a similar shape and dimensions, but the tip of the needle has a sharp end which is suitable for piercing a closure of a vessel.

Although preferred embodiments have been described using specific terms, such description is for illustrative purposes only, and it is to be understood that changes and variations may be made without departing from the spirit or scope of the following claims.

The invention claimed is:

1. A method for dispensing a liquid volume into a vessel by means of a pipetting needle and without any contact between the needle and a liquid contained in the vessel, the method comprising:

(a) forming a drop at a delivery tip of the pipetting needle, the drop being retained at the delivery tip by adhesion forces; and (b) ejecting the drop from the delivery tip by focusing a mechanical wave at the delivery tip, the focusing being achieved by applying an electrical excitation pulse signal to an electromechanical transducer for mechanically exciting the pipetting needle with a pulse of mechanical waves that propagate through a tubular wall of the needle, wherein the pulse includes pulses of several modes of propagation, each having an individual dispersion characteristic, focused and superimposed at the tip of the pipetting needle.

2. The method of claim 1 wherein the electrical excitation pulse signal is predetermined by:

(a) simulating by means of a finite difference method propagation of a mechanical pulse through a wall of a portion of a pipetting needle that has the shape of capillary tube, in simulation, the pulse being applied at a location corresponding to a location where the pulse of mechanical waves is to be generated in reality for ejecting a drop;

(b) recording a simulated electrical pulse signal corresponding to the simulated mechanical pulses; and (c) calculating the electrical excitation pulse signal to be applied in reality to said electromechanical transducer by time reversal of the recorded signal obtained in step (b).

3. A micropipetting apparatus for dispensing a liquid volume into a vessel comprising:

(a) a pipetting needle having a first end comprising a delivery tip, a second end connected to a pressure source, and a middle portion extending between the first end and the second end;

(b) an electromechanical transducer mechanically connected with the second end of the pipetting needle;

(c) an electrical signal generator for generating an electrical excitation pulse signal and for applying this signal to the electromechanical transducer for mechanically exciting the pipetting needle with a pulse of mechanical waves that propagate through a tubular wall of the needle, wherein the pulse includes pulses of several modes of propagation, each having an individual dispersion characteristic, focused and superimposed at the tip of the pipetting needle, thereby causing ejection of a drop formed on the delivery tip of the pipetting needle without any contact between the pipetting needle and a liquid contained in the vessel.

4. The micropipetting apparatus according to claim 3, wherein the electrical excitation pulse signal is adapted to length and dispersion characteristics of the pipetting needle.

5. The micropipetting apparatus according to claim 3, wherein the electromechanical transducer is a piezoelectric transducer.

6. The micropipetting apparatus according to claim 5, wherein the electrical excitation pulse signal applied to the piezoelectric transducer is configured to cause a mainly radial displacement of liquid within the needle.

7. The micropipetting apparatus according to claim 5, wherein the electrical excitation pulse signal applied to the piezoelectric transducer is configured to cause a mainly axial displacement of liquid within the needle.

8. The micropipetting apparatus according to claim 5, wherein the piezoelectric transducer is radially polarized.

9. The micropipetting apparatus according to claim 8, wherein the electrical excitation pulse signal applied to the piezoelectric transducer is configured to cause a mainly radial displacement of liquid within the needle.

10. The micropipetting apparatus according to claim 8, wherein the electrical excitation pulse signal applied to the piezoelectric transducer is configured to cause a mainly axial displacement of liquid within the needle.

11. The micropipetting apparatus according to claim 5, wherein the piezoelectric transducer is axially polarized.

12. The micropipetting apparatus according to claim 11, wherein the electrical excitation pulse signal applied to the piezoelectric transducer is configured to cause a mainly radial displacement of liquid within the needle.

13. The micropipetting apparatus according to claim 11, wherein the electrical excitation pulse signal applied to the piezoelectric transducer is configured to cause a mainly axial displacement of liquid within the needle.

* * * * *

UNITED STATES PATENT AND TRADEMARK OFFICE
CERTIFICATE OF CORRECTION

PATENT NO. : 7,615,378 B2
APPLICATION NO. : 11/128677
DATED : November 10, 2009
INVENTOR(S) : Dual et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 922 days.

Signed and Sealed this

Fourteenth Day of December, 2010

David J. Kappos
*Director of the United States Patent and Trademark Office*